US00PP29047P3

(12) United States Plant Patent
Brazelton et al.

(10) Patent No.: US PP29,047 P3
(45) Date of Patent: Mar. 6, 2018

(54) BLUEBERRY PLANT NAMED 'ZF08-070'

(50) Latin Name: *Vaccinium corymbosum*
Varietal Denomination: ZF08-070

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/330,668

(22) Filed: Oct. 25, 2016

(65) Prior Publication Data

US 2017/0118883 P1 Apr. 27, 2017

Related U.S. Application Data

(60) Provisional application No. 62/285,377, filed on Oct. 27, 2015.

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Hahn Loeser & Parks, LLP-San Diego

(57) ABSTRACT

The new blueberry plant variety 'ZF08-070' is a multi-purpose commercial variety intended for the fresh or processed fruit markets. The new blueberry plant originated from a cross of 'Legacy' (female parent) by 'Draper' (male parent, U.S. Plant Pat. No. 15,103). The variety has excellent plant vigor, an upright plant habit, ripens fruit mid-season, and produces a large berries with uniform size and light blue color. 'ZF08-070' was selected for its upright habit, consistent berry size, cold hardiness, and vigor.

8 Drawing Sheets

CROSS REFERENCE TO RELATED APPLICATIONS

This application claims the benefit of U.S. Provisional Patent Application No. 62/285,377 filed on Oct. 27, 2015, which is incorporated herein by reference in its entirety as though fully set forth.

Latin name of the family, genus, and species: Family—Ericaceae. Genus—*Vaccinium*. Species—*corymbosum*.

Variety denomination: The new blueberry plant claimed is of the variety denominated 'ZF08-070'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L.) plant, referred to as 'ZF08-070', as herein described and illustrated. The new blueberry plant variety 'ZF08-070' is a multi-purpose commercial variety intended for the fresh or processed fruit markets. The variety has excellent plant vigor, an upright plant habit, ripens fruit mid-season, and produces a large berries with uniform size and light blue color. 'ZF08-070' was selected for its upright habit, consistent berry size, cold hardiness, and vigor. The mid-season blueberry cultivar 'Bluecrop' has historically dominated the Pacific Northwest growing region due to its consistently high fruit yields, but 'Bluecrop' acreage is being gradually replaced with newer cultivars such as 'Draper' that possess better fruit quality. 'Draper' produces a fruit which is more firm than 'Bluecrop' and also has more uniform fruit coloration. However, 'Draper' plants are not as vigorous, disease tolerant, or adaptable to cold climates and heavy soils as 'Bluecrop'. Thus, there is a need in the Pacific Northwest and other northern highbush blueberry growing regions for a variety that combines better fruit quality than 'Bluecrop' with better vigor and adaptability than 'Draper'. 'ZF08-070' possesses these qualities and may be of value to the commercial blueberry industry in the Pacific Northwest and other blueberry production regions where northern highbush blueberries are grown.

SUMMARY OF THE INVENTION

Pedigree and History: The new blueberry plant originated from a cross of 'Legacy' (female parent) by 'Draper' (male parent, U.S. Plant Pat. No. 15,103).

The cross that produced 'ZF08-070' (denominated by the cross code 'X04-044') was made in Lowell, Oreg., USA in 2004.

The new blueberry plant variety 'ZF08-070' was initially propagated by softwood cuttings in 2008. Rooted plants from these cuttings were field planted in Lowell, Oreg., USA in 2009 to establish a plot of nine plants for further observation. Additional plants have been propagated via softwood cuttings from the plants in Lowell, Oreg. to establish additional plantings in Washington, Oregon, and California, USA. The plants established in Oregon were successfully used to establish in vitro culture lines in 2011. Plants derived from the in vitro cultures were used to establish additional research plantings for observation and yield data collection in Washington and Oregon.

The seedling family that produced 'ZF08-070' was initially grown in 50 cell propagation trays and field planted in 2005 at the Fall Creek research farm in Lowell, Oreg. 'ZF08-070' was selected in 2008 because it had large yields of fruit, with good firmness, light blue color, large size, and good storage quality. After being selected in the seedling planting, 'ZF08-070' was propagated by softwood cuttings and a nine plant plot was established in Lowell, Oreg. The nine plant plot was evaluated for plant performance, fruit quality and yield in comparison to the standard varieties 'Draper' and 'Legacy' beginning in April, 2011. Beginning in 2009, additional observational plots were established in commercial blueberry fields located near Lynden, Wash., Paterson, Wash., and Stockton, Calif., USA and Segovia, Spain. Additional observational plots using plants derived from tissue culture were also established in Washington and Oregon in 2014. After extensive evaluation throughout the Pacific Northwest and other blueberry growing regions, 'ZF08-070' was determined to be consistently vigorous, tolerant of heavy soils, and tolerant of damaging winter minimum temperatures or poor adaptation to northern latitudes that caused yield losses in field trials with other northern highbush cultivars and selections.

The new blueberry plant 'ZF08-070' is distinguished by an upright growth habit, excellent vigor, large leaves, reddish new wood, cylindrical corollas with a broad aperture, reddish purple or reddish yellow fall leaf color, and large fruit with a light blue color and a spheroid or slightly flattened shape. The following characteristics of the new cultivar have been repeatedly observed and can be used to distinguish 'ZF08-070' as a unique *Vaccinium corymbosum* hybrid plant:

1) Fruit that is globose or slightly oblate, light blue in color, and uniformly large in size
2) Reddish colored new wood on one year old canes
3) Broad corollas that are typically cylindrical in form, with a wide corolla aperture
4) Excellent plant vigor even on heavy soils
5) Balanced distribution of fruit buds and vegetative buds on canes, resulting in a plant that is easy to prune and capable of consistently producing uniformly large fruit
6) Large leaves with an acuminate tip and purple, red or yellow fall color
7) Upright or erect plant growth habit
8) Large diameter canes with relatively few laterals and relatively little branching
9) Loose clusters of fruit located on the outside of the plant, facilitating harvest Plants of 'ZF08-070' propagated from softwood cuttings or in vitro are phenotypically stable and exhibit the same characteristics as the original plant. Plants of 'ZF08-070' are phenotypically distinct from either of its parents, 'Legacy' and 'Draper'. The parent 'Legacy' has a plant that is more branched and less upright in form. The leaves of 'Legacy' are slightly more narrow than 'ZF08-070'. Leaves of 'Legacy' are more flattened in profile than 'ZF08-070', 'ZF08-070' leaves are more undulate or revolute than 'Legacy'. Plants of 'Legacy' also form fewer buds on one year old canes than plants of 'ZF08-070'. Compared to the parent 'Draper', plants of 'ZF08-070' are more vigorous and taller in stature at maturity. Plants of 'Draper' have more numerous canes than 'ZF08-070' and the canes of 'Draper' have a smaller average diameter than canes of 'ZF08-070'. 'Draper' fruit is more flattened (oblate) in shape than fruit of 'ZF08-070'. 'Draper' leaves also have a margin that is more undulate (wavy) than leaves of 'ZF08-070'.

DETAILED BOTANICAL DESCRIPTION

Figure 1:
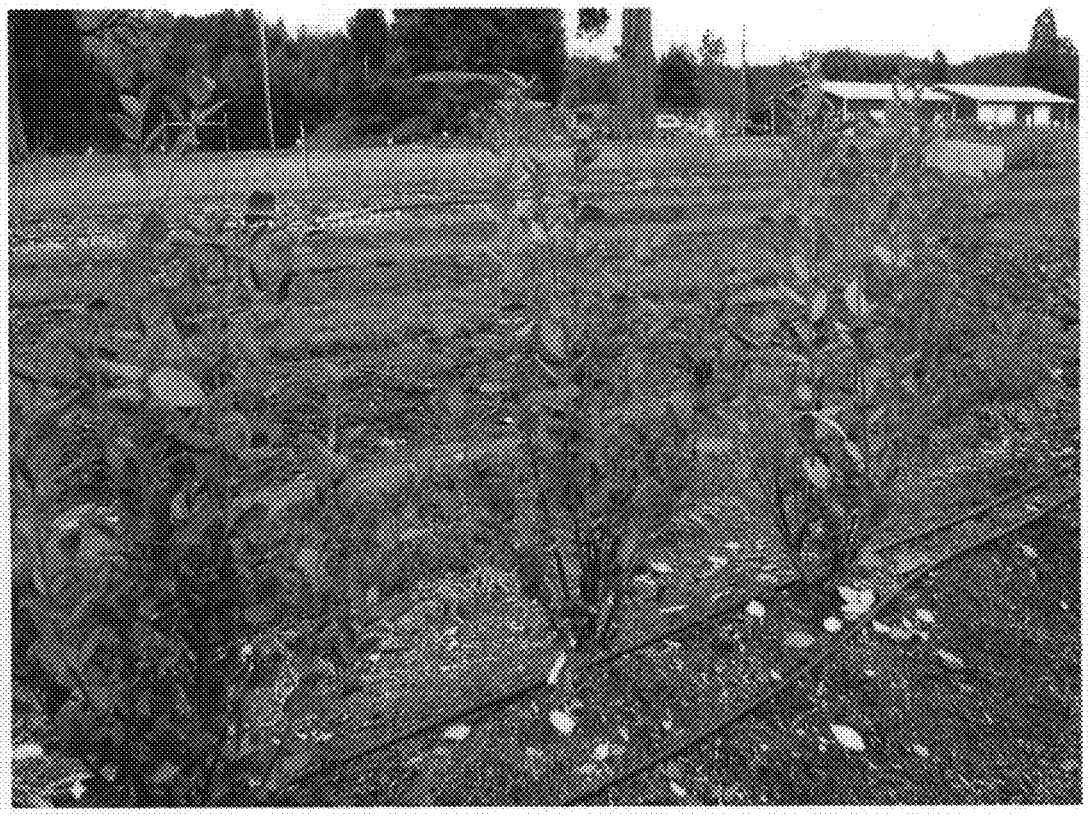
FIG. 1 is a photograph of the plant of the new variety in fall, showing the fall color and plant growth habit. The plants were grown in Lowell, Oreg. and photographed on Dec. 8, 2014.
Figure 2:
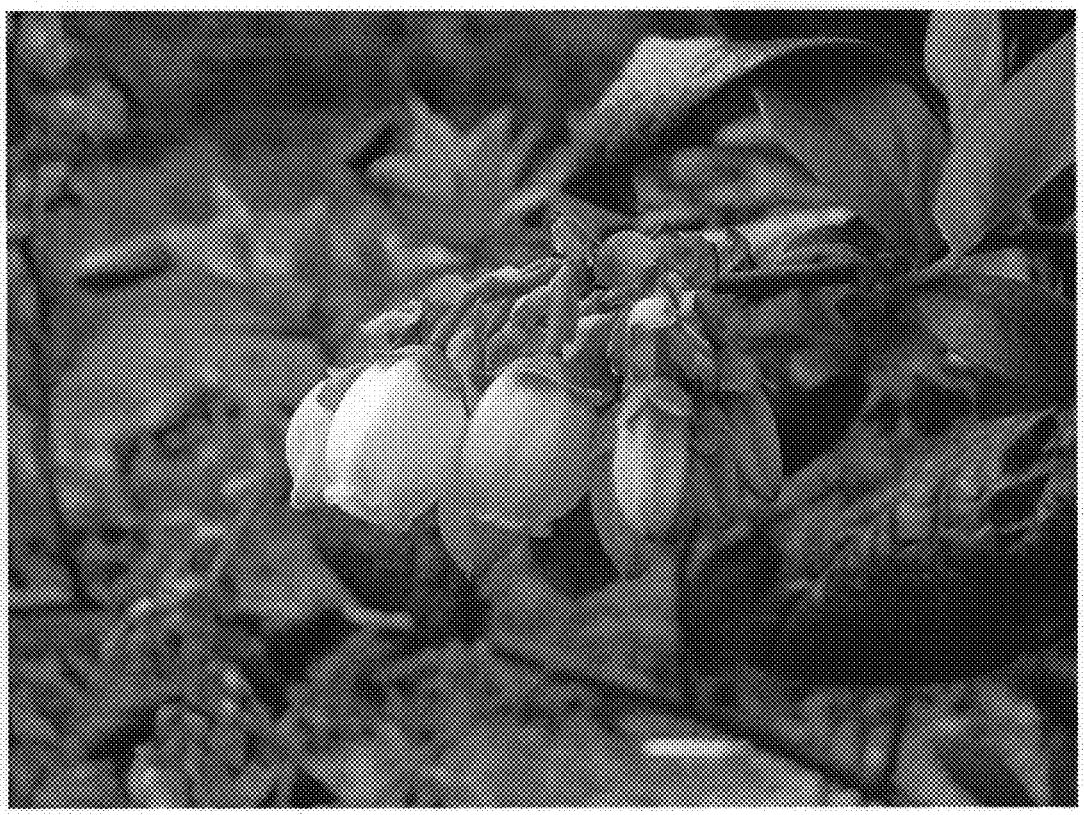
FIG. 2 is a photograph of flowers of the new variety grown in Lowell, Oreg., and photographed on Apr. 12, 2013.
Figure 3:
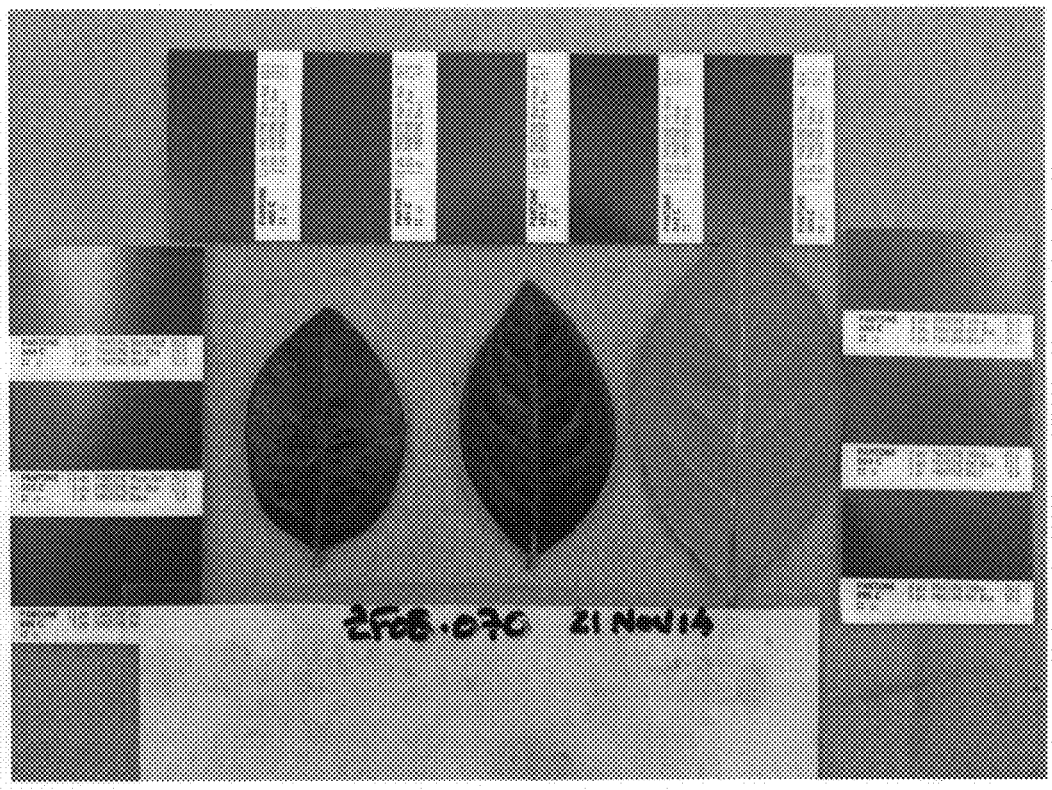
FIG. 3 is a photograph of the leaves of the new variety grown in Lowell, Oreg. and photographed on Nov. 21, 2014.
Figure 4:
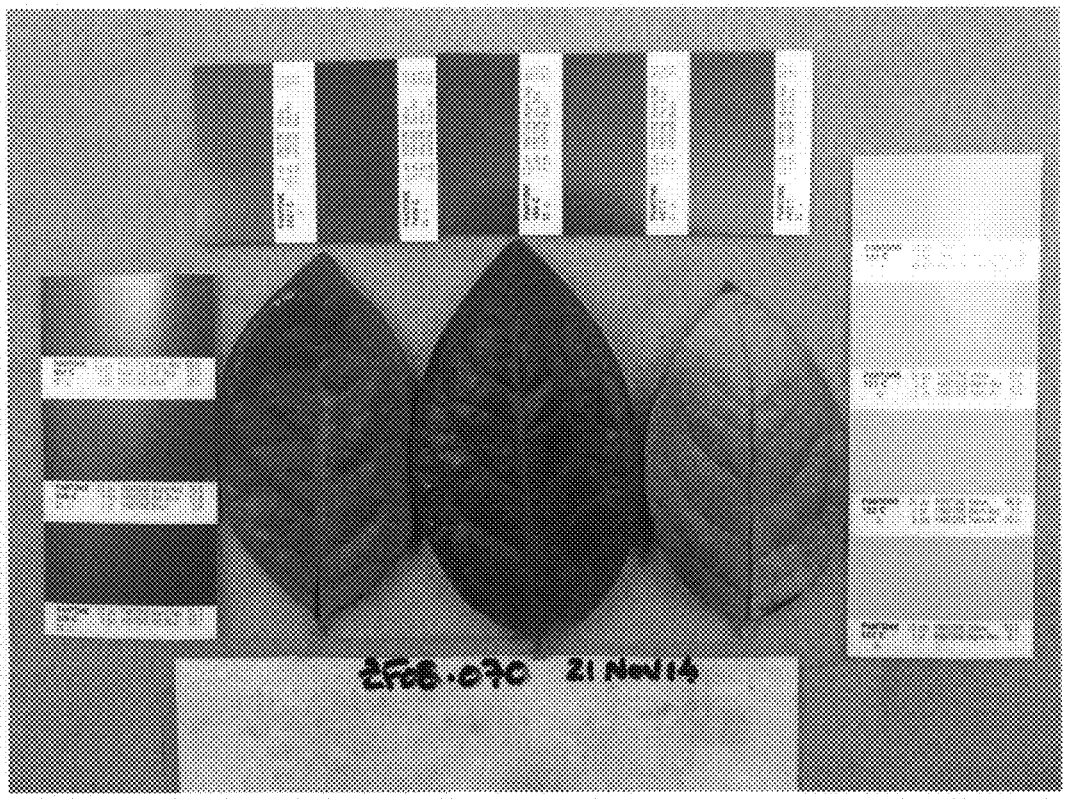
FIG. 4 is a photograph of the fall color on leaves of the new variety grown in Lowell, Oreg. and photographed on Nov. 21, 2014.
Figure 5:
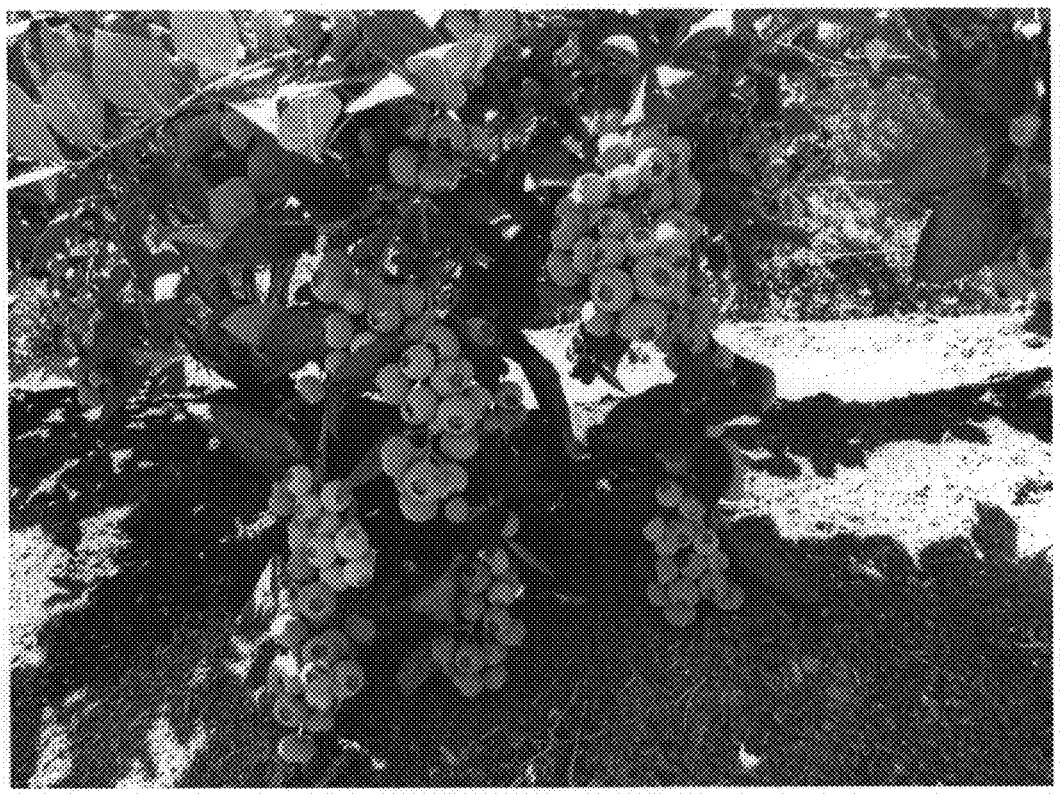
FIG. 5 is a photograph of a cluster of fruit of the new variety grown in Lowell, Oreg. and photographed on Jul. 17, 2013.
Figure 6:
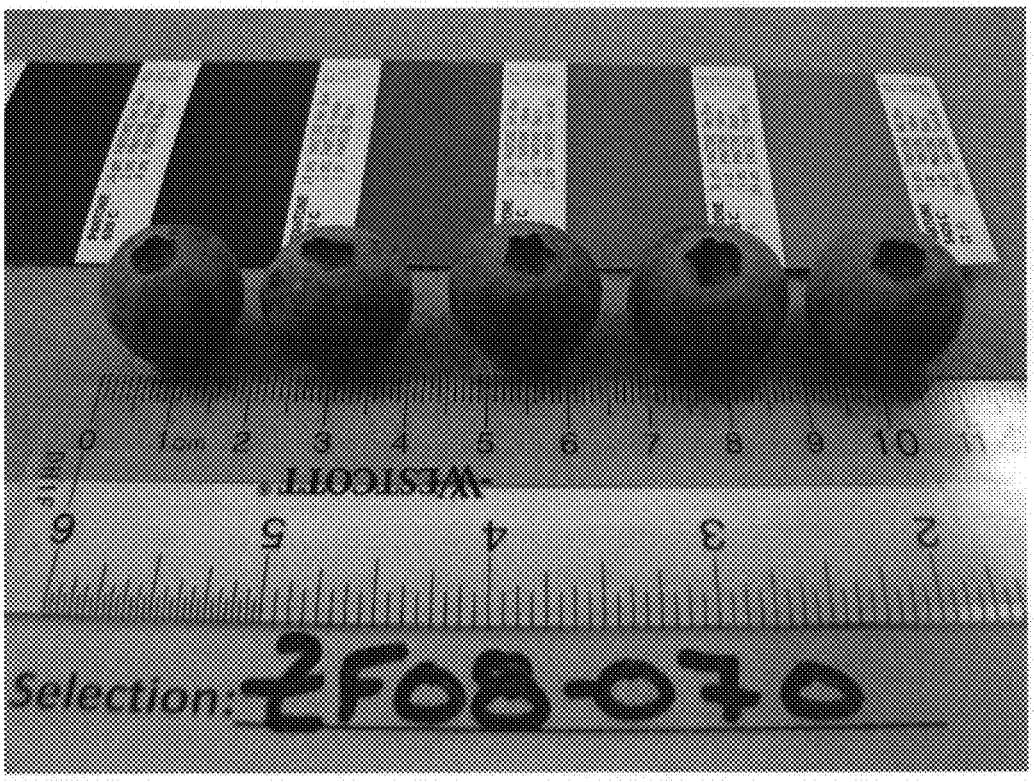
FIG. 6 is a photograph of the calyx side of fruit of the new variety grown in Lowell, Oreg. and photographed on Aug. 1, 2013.
Figure 7:
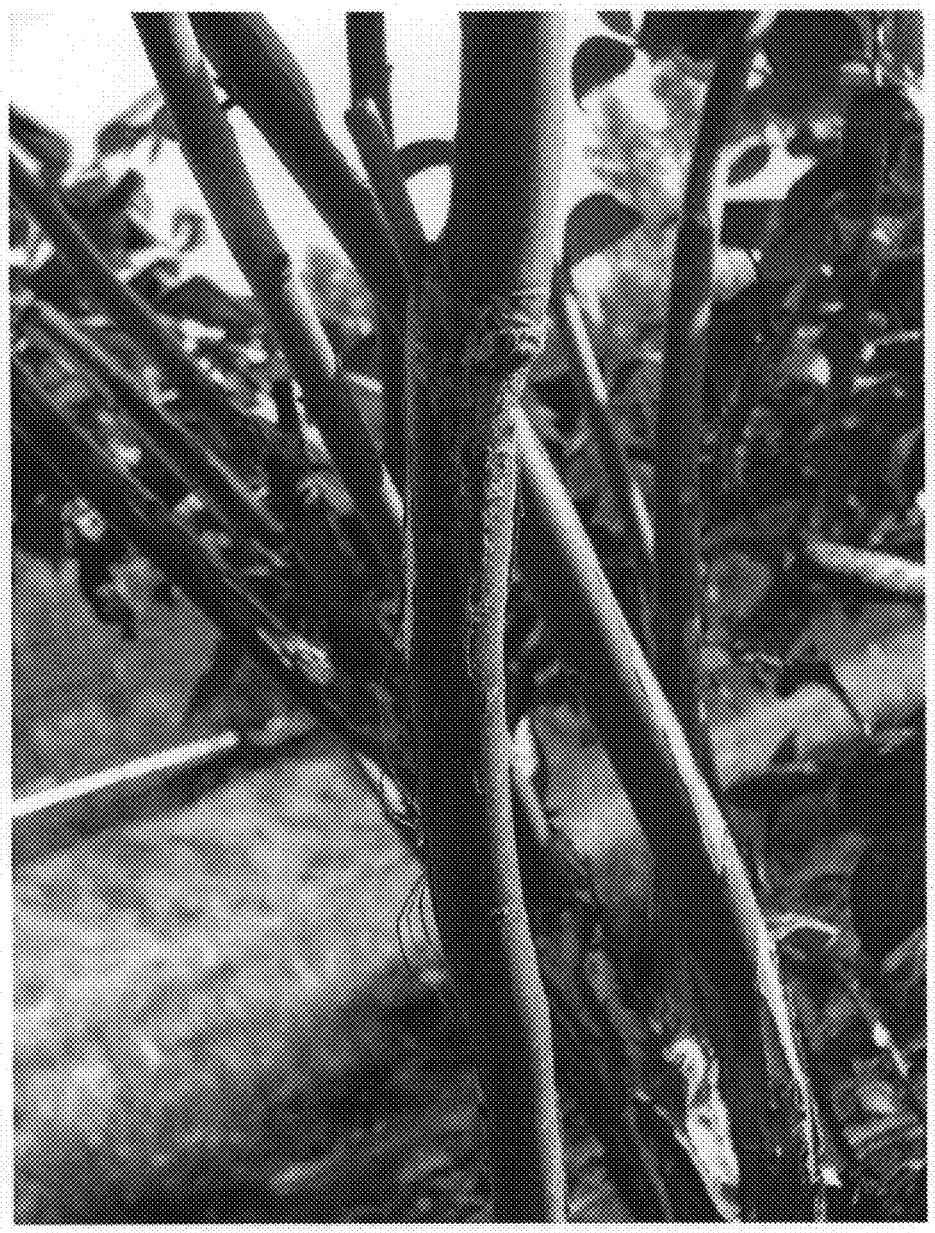
FIG. 7 is a photograph of one year canes of the new variety, grown in Lowell, Oreg. and photographed on Nov. 7, 2012.
Figure 8:
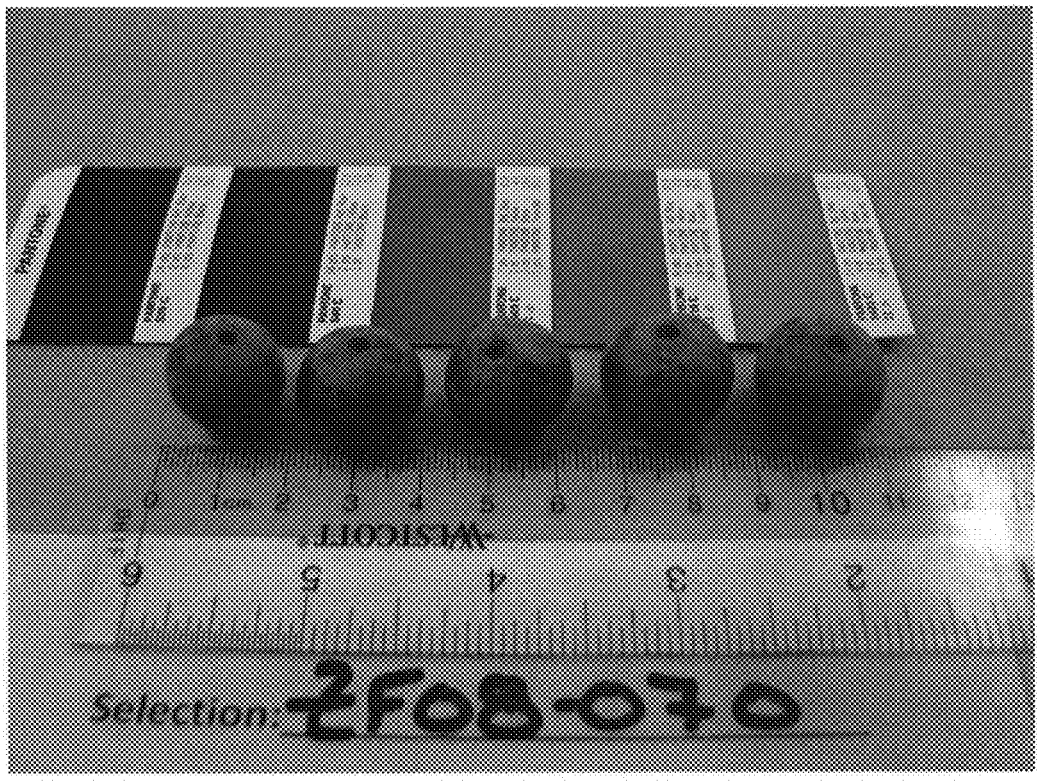
FIG. 8 is a photograph of the fruit of the new variety.

The following detailed description sets forth the distinctive characteristics of 'ZF08-070'. The data which define these characteristics were collected from asexual reproductions of the original selection. Dimensions, sizes, colors, and other characteristics are approximations and averages set forth as accurately as possible. The plant history was taken on plants approximately 4 years of age, and the descriptions relate to plants grown in the field located at 39252 Jasper-Lowell Rd, Lowell, Oreg. Descriptions of fruit characteristics were made on fruit grown in 2013 at the field described above. Color designations are from "The Pantone Book of Color" (by Leatrice Eiseman and Lawrence Herbery, Harry N. Abrams, Inc., Publishers, New York 1990). Where the Pantone color designations differ from the colors in the photographs, the Pantone colors are accurate.

VARIETY

Classification:

*a. Family.*—Ericaceae.

*b. Genus.*—*Vaccinium.*

*c. Species.*—*corymbosum.*

*d. Common name.*—Northern Highbush Blueberry.

Parentage:

*a. Female parent.*—'Legacy' (unpatented).

*b. Male parent.*—'Draper' (U.S. Plant Pat. No. 15,103).

Market class: Fresh market or individual quick frozen berries.

PLANT

General:

a. *Parentage*.—Female parent 'Legacy' (unpatented), male parent Draper (U.S. Plant Pat. No. 15,103).
b. *Plant height*.—Average 1 meter.
c. *Plant width*.—Average 1 meter.
d. *Growth habit*.—Upright, round.
e. *Plant vigor*.—Vigorous.
f. *Productivity*.—In Lowell, Oreg. on 2 year old plants 1.12 lbs per plant, compared to Draper plants of the same age which produced an average of 2.39 lbs per plant. On 3 year old plants 4.25 lbs per plant, compared to Draper plants of the same age, which produced an average of 4.54 lbs per plant. On 4 year old plants 7.95 lbs per plant, compared to Draper plants of the same age which produced an average of 4.29 lbs per plant.
g. *Suitability for mechanical harvesting*.—Good.
h. *Cold hardiness*.—Based on pedigree, approximately USDA zone 4. Tested up to USDA zone 6.
i. *Chilling requirement*.—Minimum of 1000 hours below 45 degrees Fahrenheit.
j. *Leafing*.—Good.
k. *Twigginess*.—Low.
l. *Resistance/susceptibility to root rot* (*Phytopthora cinnamomii*).—Good tolerance to *Phytopthora* based on anecdotal field observations and a controlled inoculation trial performed at Oregon State University by John Yeo.
m. *Resistance/susceptibility to stem blight* (*Botryosphaeria* sp.).—None noted.
n. *Resistance/susceptibility to Phomopsis twig blight* (*Phomopsis vaccinii*).—None noted.
o. *Resistance/susceptibility to Botrytis* (*Botrytis cinerea*).—Good tolerance to *Botrytis* based on anecdotal field observations.
p. *Resistance/susceptibility to leaf spot* (*Septoria* spp.).—No susceptibility noted.
q. *Resistance/susceptibility to leaf rust* (*Naohidemyces vaccinii*).—Good tolerance to Leaf Rust based on anectdotal field observations.
r. *Resistance/susceptibility to bud mites* (*Acalatus vaccinii*).—None noted.

STEM

General:

a. *Suckering tendency*.—Low.
b. *Mature cane color*.—Pantone colors Raw Umber 17-1422, Shell 13-1405 and Mineral Red 17-1537.
c. *Mature cane length*.—Average 19 in.
d. *Mature cane width*.—Average 1.5 cm.
e. *Bark texture*.—Rough.
f. *Fall color on new shoots*.—Pantone colors Red Earth 18-1444 and Green Banana 14-0434 to Celery Green 13-0532.
g. *Surface texture of new wood*.—Smooth.
h. *Internode length on strong, new shoots*.—Average 17.85 mm.
i. *Average number of buds per fruiting lateral*.—7.

FOLIAGE

General:

a. *Time of beginning of leaf bud burst*.—In Lowell, Oreg. late March to early April.
b. *Leaf color* (*upper surface*).—a. Mature leaves Pantone Chive 19-0323. b. New leaves Pantone Sierra 18-1239 and Deep Olive 18-0527.
c. *Leaf color* (*lower surface*).—Pantone color Epsom 17-0324.
d. *Leaf arrangement*.—Alternate.
e. *Leaf shape*.—Elliptic.
f. *Leaf margins*.—Entire.
g. *Leaf venation*.—Pinnate.
h. *Leaf apices*.—Acute.
i. *Leaf bases*.—Vary from rounded to acute.
j. *Leaf length*.—Average 60.03 mm.
k. *Leaf width*.—Average 33.4 mm.
l. *Leaf length/width ratio*.—1.80 (wide leaves).
m. *Leaf nectaries*.—Absent.
n. *Pubescence of upper side*.—Absent.
o. *Pubescence of lower side*.—Absent.
p. *Cross sectional profile*.—Flat or slightly revolute.
q. *Longitudinal profile*.—Slightly undulate.
r. *Attitude*.—Ascending (acute).
s. *Fall leaf color*.—Pantone Barn Red 18-1531, Pantone Catchup 18-1449, Pantone Burgundy 19-1617, Pantone Spectra Yellow 14-0957.

Petioles:

a. *Length*.—Average 2.65 mm.
b. *Width*.—Average 1.75 mm.
c. *Color*.—Pantone color Green Olive 17-0535.
d. *Surface texture*.—Smooth.

FLOWERS

General:

a. *Time of beginning of flowering*.—Approximately mid-April in Lowell, Oreg.
b. *Time of* 50% *anthesis*.—Approximately late April in Lowell, Oreg.
c. *Flower shape*.—Cylindrical to slightly urceolate.
d. *Flower fragrance*.—Faint, sweet.
e. *Immature flower color*.—Pantone colors Holly Berry 17-1633, Snow White 11-0602 and Mellow Green 12-0426.
f. *Pollen staining*.—Approximately 95% viable staining with 2% acetocarmine dye.
g. *Self-compatibility*.—Very good. Approximately 73% of self-pollinated flowers reached maturity on self-compatibility pollination trials, compared to 80% of flowers reached maturity when pollinated with pollen of the variety 'Liberty'.

Corolla:

a. *Color*.—Pantone color Snow White 11-0602.
b. *Length*.—Average 9.7 mm.
c. *Width*.—Average 9.3 mm.
d. *Aperture width*.—Average 5.24 mm.
e. *Anthocyanin coloration of corolla at time of anthesis*.—Low.
f. *Corolla ridges*.—Present but not very distinct.
g. *Protrusion of stigma*.—Average −0.2 mm below lip of corolla.

Inflorescence:

*a. Length.*—Variable, average of 54.91 mm.

*b. Diameter.*—Variable, average of 19.35 mm.

*c. Length of peduncle.*—Variable, averaging 35.56 mm.

*d. Surface texture of peduncle.*—Smooth.

*e. Color of peduncle.*—Pantone colors Mellow Green 12-0426 and Mineral Red 17-1537.

*f. Length of pedicel.*—Average 9.65 mm.

*g. Surface texture of pedicel.*—Smooth.

*h. Color of pedicel.*—Pantone color Peridot 17-0336.

*i. Number of flowers per cluster.*—Average 10-13.

*j. Flower cluster density.*—Moderate to high.

Calyx (with sepals):

*a. Diameter.*—Average 5.8 mm.

*b. Color (sepals).*—Pantone colors Peridot 17-0336 and Water Cress 17-0220.

*c. Calyx surface.*—Smooth.

Stamen:

*a. Length.*—Data not collected.

*b. Number per flower.*—10.

*c. Filament color.*—Data not collected.

Pistil:

*a. Length.*—8.18 mm.

*b. Ovary color (exterior).*—Pantone color Peridot 17-0336.

*c. Style: length.*—Data not collected.

Anther:

*a. Length.*—5.08 mm.

*b. Number.*—10.

*c. Color.*—Pantone colors Adobe 17-1340 and Autumn Leaf 17-1347.

Pollen:

*a. Abundance.*—Moderate.

*b. Color.*—Pantone color Pale Banana 12-0824.

FRUIT

General:

*a. Time of fruit ripening.*—Approximately early July through late July in Lowell, Oreg.

*b. Time of 50% maturity.*—Approximately mid-July in Lowell, Oreg.

*c. Fruit development period.*—Averages 17 days in Lowell, Oreg.

*d. Mean harvest date.*—July 19.

*e. Mean date last pick.*—August 6.

*f. Cluster density.*—Moderate to high.

*g. Berries per cluster.*—Approximately 7-12 berries per cluster.

*h. Unripe fruit color.*—Pantone colors Oasis 16-0540 and Maroon 18-1619.

*i. Ripe berry color.*—Pantone colors Dapple Gray 16-3907 and Crown Blue 19-3926.

*j. Berry skin color after polishing.*—Pantone color Shale 19-3903.

*k. Berry surface wax abundance.*—Moderately abundant and moderately persistant.

*l. Berry flesh color.*—Pantone color Winter White 11-0507.

*m. Berry weight.*—Average 2.5 g per berry, 5 year average from 2011-2015 compared to Draper fruit from plants of the same age, which were an average size of 1.96 g.

*n. Berry height from calyx to scar.*—Average 13.54 mm.

*o. Berry diameter.*—Average 19.92 mm.

*p. Calyx aperture.*—Average 5.38 mm.

*q. Calyx depth.*—Average 1.83 mm.

*r. Pedicel length.*—Average 10.42 mm.

*s. Pedicel surface texture.*—Smooth.

*t. Berry detachment force.*—Easy.

*u. Berry shape.*—Oblate to round.

*v. Fruit stem scar.*—Small and dry. Average diameter of 1.41 mm.

*w. Berry flavor.*—Balanced.

*x. Sweetness when ripe.*—Moderate to high.

*y. Firmness when ripe.*—Moderately firm.

*z. Acidity when ripe.*—Low.

*aa. Storage quality.*—Very good.

*bb. Uses.*—Fresh market fruit production, machine harvest individual quick frozen fruit production.

SEED

General:

*a. Seed abundance in fruit.*—Average 30 seeds per berry.

*b. Seed color.*—Pantone color Carob Brown 18-1229.

*c. Seed dry weight.*—Approximately 0.5 mg per seed.

*d. Seed length.*—Average 1.51 mm.

COMPARISON BETWEEN PARENTAL AND COMMERCIAL CULTIVARS

| Denomination of similar variety | Characteristic for comparison | State of expression of similar variety | State of expression of candidate variety (ZF08-070) |
|---|---|---|---|
| Legacy | Fruit size | 1.86 g (Large) | 2.50 g (Very Large) |
| Draper | Fruit Size | 1.96 g (Large) | 2.50 g (Very Large) |
| Draper | Evergreen/leaf persistence in fall | Fully deciduous in Lowell, OR | Partly evergreen in Lowell, OR |
| Draper | Plant vigor | Low to medium | High |
| Legacy | Leaf margin: profile | Plane (flat) | Undulate (wavy) |
| Draper | Fruit shape | Oblate | Slightly oblate |

The invention claimed is:

1. A new and distinct variety of blueberry plant named 'ZF08-070' substantially as illustrated and described herein.

* * * * *